(12) United States Patent
Weeratunga et al.

(10) Patent No.: US 9,382,233 B2
(45) Date of Patent: Jul. 5, 2016

(54) FORMS OF VILAZODONE AND PROCESSES FOR THE PREPARATION THEREOF

(71) Applicant: APOTEX INC., Toronto (CA)

(72) Inventors: Gamini Weeratunga, Ancaster (CA); Murali Kondamreddy, Brantford (CA); Allan W. Rey, Brantford (CA); Cameron L. McPhail, Brantford (CA); Yajun Zhao, Brantford (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 14/408,257

(22) PCT Filed: Jun. 13, 2013

(86) PCT No.: PCT/CA2013/000560
§ 371 (c)(1),
(2) Date: Dec. 15, 2014

(87) PCT Pub. No.: WO2013/185209
PCT Pub. Date: Dec. 19, 2013

(65) Prior Publication Data
US 2015/0175583 A1    Jun. 25, 2015

Related U.S. Application Data

(60) Provisional application No. 61/659,425, filed on Jun. 13, 2012, provisional application No. 61/754,197, filed on Jan. 18, 2013.

(51) Int. Cl.
*C07D 405/14* (2006.01)
*A61K 31/496* (2006.01)
*C07D 405/12* (2006.01)

(52) U.S. Cl.
CPC .................................. *C07D 405/12* (2013.01)

(58) Field of Classification Search
CPC ............................. A61K 31/496; C07D 405/14
USPC ....................................... 544/373; 514/254.09
See application file for complete search history.

(56) References Cited

U.S. PATENT DOCUMENTS

| 5,532,241 | A | 7/1996 | Bottcher et al. |
| 7,834,020 | B2 | 11/2010 | Bathe et al. |
| 8,835,635 | B2 * | 9/2014 | Mohan Rao ......... C07D 405/14 544/373 |
| 2007/0099933 | A1 | 5/2007 | Heinrich et al. |
| 2013/0324554 | A1 | 12/2013 | Mohan Rao et al. |
| 2014/0179713 | A1 | 6/2014 | Dwivedi et al. |

FOREIGN PATENT DOCUMENTS

| CN | 102977083 A | 3/2013 |
| WO | 0072832 A2 | 12/2000 |
| WO | 02102794 A2 | 12/2002 |
| WO | 2012131706 A1 | 10/2012 |
| WO | 2013078361 A1 | 5/2013 |
| WO | 2013088373 A1 | 6/2013 |
| WO | 2013156935 A1 | 10/2013 |
| WO | 2013164794 A1 | 11/2013 |
| WO | 2013168126 A1 | 11/2013 |
| WO | 2013175499 A2 | 11/2013 |
| WO | 2013182946 A2 | 12/2013 |
| WO | 2014028473 A1 | 2/2014 |
| WO | 2014064715 A2 | 5/2014 |
| WO | 2014087428 A1 | 6/2014 |

OTHER PUBLICATIONS

"The synthesis and polymorphic form of ethyl 5-(4-(4-(5-cyano-1H-indol-3-yl)butyl)piperazin-1-yl)benzofuran-2-carboxylate hydrochloride", IP.com Disclosure No. IPCOM000213557D (2011).

* cited by examiner

*Primary Examiner* — Golam M M Shameem
(74) *Attorney, Agent, or Firm* — The Webb Law Firm (57) ABSTRACT

Vilazodone hydrochloride benzyl alcohol solvates are provided as well as processes for the preparation thereof.

10 Claims, 4 Drawing Sheets

FORMS OF VILAZODONE AND PROCESSES FOR THE PREPARATION THEREOF

TECHNICAL FIELD

The present invention relates to a solvate of Vilazodone and processes for the preparation thereof.

BACKGROUND

Vilazodone hydrochloride, 1, has the chemical name 2-benzofurancarboxamide, 5-[4-[4-(5-cyano-1H-indol-3-yl) butyl]-I-piperazinyl], hydrochloride (1:1). It is marketed in the U.S. as Viibryd® and is indicated for the treatment of major depressive disorder.

U.S. Pat. No. 5,532,241 and WO 00/72832 teach 1-[4-(5-Cyanoindol-3-yl)butyl]-4-(2-carbamoyl-benzofuran-5-yl)-piperazine, physiologically acceptable salts thereof, processes for preparation thereof and uses in treating certain medical disorders.

U.S. Pat. No. 7,834,020 discloses crystalline modifications of the hydrochloride of 1-[4-(5-cyanoindol-3-yl)butyl]-4-(2-carbamoyl-benzofuran-5-yl)-piperazine, crystalline modification of the dihydrochloride of 1-[4-(5-cyanoindol-3-yl)butyl]-4-(2-carboamoyl-benzofuran-5-yl)-piperazine and amorphous 1-[4-(5-cyanoindol-3-yl)butyl]-4-(2-carbamoyl-benzofuran-5-yl)-piperazine hydrochloride which are suitable in particular for the preparation of solid medicaments for the treatment or prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypogonadism, secondary amenorrhea, premenstrual syndrome and undesired puerperal lactation.

SUMMARY

The present invention relates, at least in part, to a crystalline benzyl alcohol solvate of vilazodone hydrochloride wherein the molar ratio of vilazodone hydrochloride to benzyl alcohol is approximately 1:0.5. The present invention also relates, at least in part, to a crystalline benzyl alcohol solvate of vilazodone hydrochloride wherein the molar ratio of vilazodone hydrochloride to benzyl alcohol is approximately 1:1. The crystalline solvates of the present invention may have advantages relative to other known forms of vilazodone hydrochloride, including chemical stability, polymorphic stability and/or varying solubility.

In illustrative embodiments of the present invention, there is provided a crystalline benzyl alcohol solvate of vilazodone hydrochloride.

In illustrative embodiments of the present invention, there is provided a crystalline benzyl alcohol solvate of vilazodone hydrochloride described herein wherein the molar ratio of vilazodone hydrochloride to benzyl alcohol is approximately 1:0.5.

In illustrative embodiments of the present invention, there is provided a Form APO-I of vilazodone hydrochloride benzyl alcohol solvate.

In illustrative embodiments of the present invention, there is provided a Form APO-I of vilazodone hydrochloride benzyl alcohol solvate described herein characterized by a PXRD diffractogram comprising peaks, in terms of degrees 2-theta, at approximately 9.5, 10.6, 13.5, 15.6, 22.3, and 26.1.

In illustrative embodiments of the present invention, there is provided a Form APO-I of vilazodone hydrochloride benzyl alcohol solvate described herein characterized by a PXRD diffractogram comprising peaks, in terms of degrees 2-theta, at approximately 5.3, 9.5, 10.6, 11.2, 13.5, 14.6, 15.6, 17.5, 19.1, 20.5, 22.3, 24.5 and 26.1.

Figure 1:
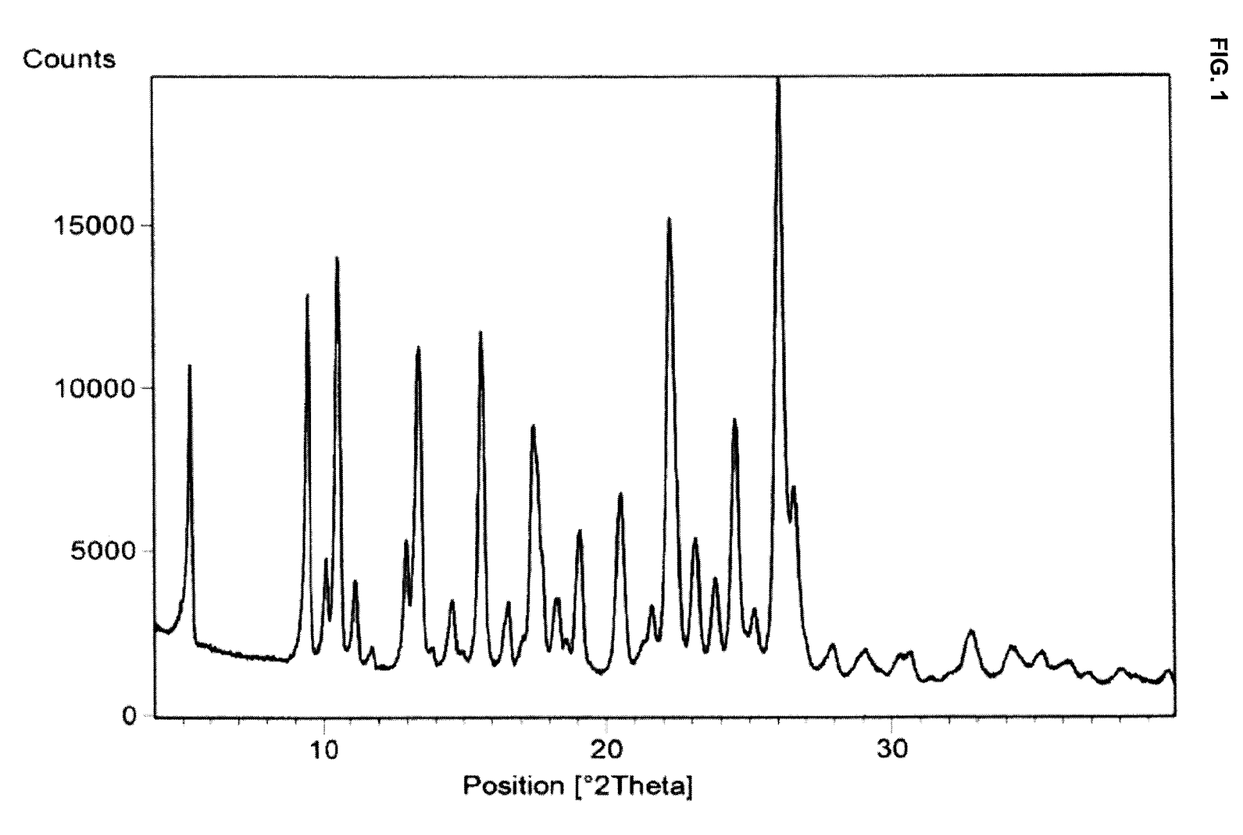
FIG. 1 is a powder X-ray diffraction (PXRD) diffractogram of APO-I

In illustrative embodiments of the present invention, there is provided a Form APO-I of vilazodone hydrochloride benzyl alcohol solvate described herein characterized by a PXRD diffractogram substantially similar to the PXRD diffractogram as depicted in FIG. 1.

In illustrative embodiments of the present invention, there is provided a Form APO-I of vilazodone hydrochloride benzyl alcohol solvate described herein characterized by a PXRD diffractogram as depicted in FIG. 1.

In illustrative embodiments of the present invention, there is provided a Form APO-I of vilazodone hydrochloride benzyl alcohol solvate described herein characterized by a 1% KBr FTIR spectrum comprising peaks, in terms of cm$^{-1}$, at approximately 2216, 1676, 1607, 1579, 1443 and 1380.

In illustrative embodiments of the present invention, there is provided a Form APO-I of vilazodone hydrochloride benzyl alcohol solvate described herein characterized by a 1% KBr FTIR spectrum comprising peaks, in terms of cm$^{-1}$, at approximately 3228, 2216, 1676, 1607, 1579, 1472, 1443 and 1380.

Figure 2:
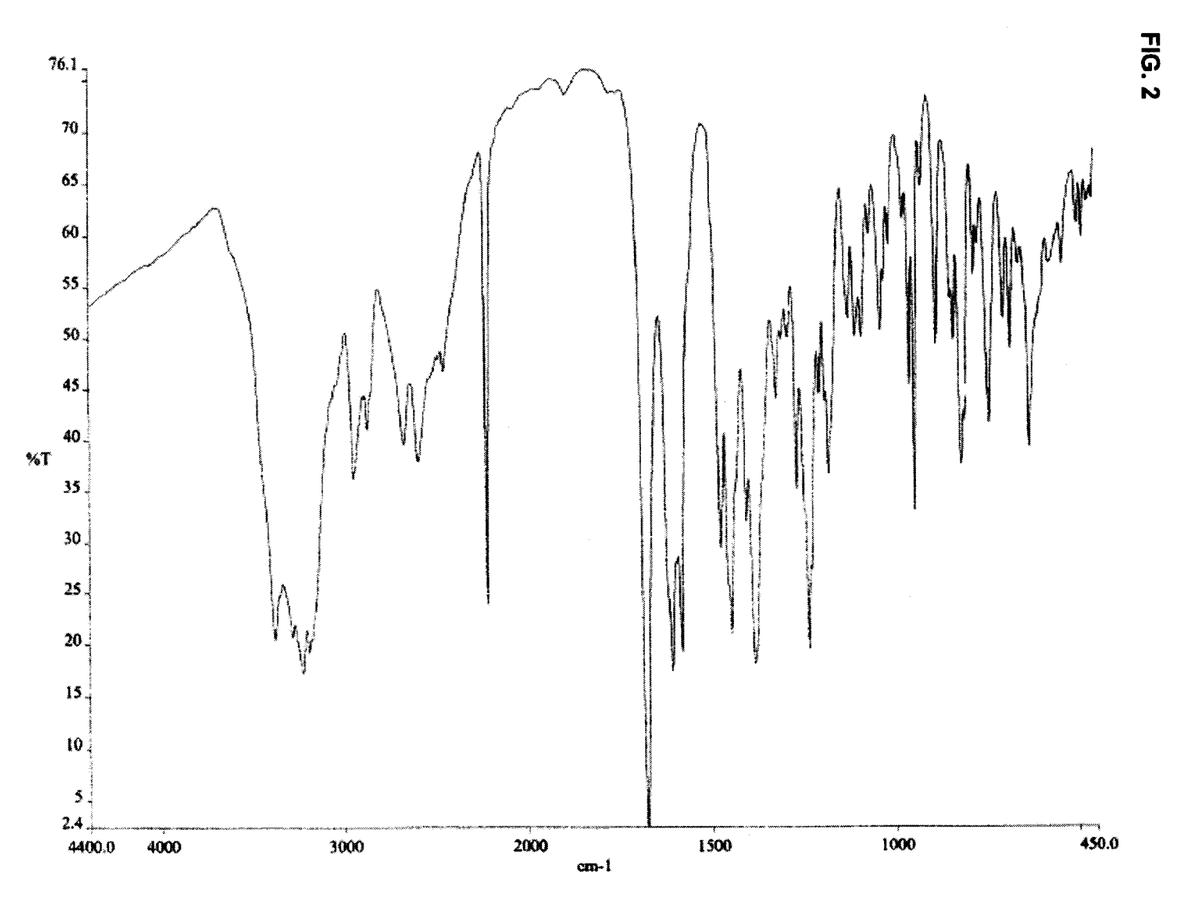
FIG. 2 is a Fourier Transform Infrared (FTIR) spectrum of APO-I

In illustrative embodiments of the present invention, there is provided a Form APO-I of vilazodone hydrochloride benzyl alcohol solvate described herein characterized by a FTIR spectrum substantially similar to the FTIR spectrum as depicted in FIG. 2.

In illustrative embodiments of the present invention, there is provided a Form APO-I of vilazodone hydrochloride benzyl alcohol solvate described herein characterized by a FTIR spectrum as depicted in FIG. 2.

In illustrative embodiments of the present invention, there is provided a pharmaceutical formulation comprising a Form APO-I vilazodone hydrochloride benzyl alcohol solvate described herein and a pharmaceutically acceptable excipient.

In illustrative embodiments of the present invention, there is provided a process for preparation of vilazodone hydrochloride benzyl alcohol solvate, the process comprising: i. preparing a first APO-I-preparation-mixture of vilazodone free base and a first APO-I-preparation-solvent, the first APO-I-preparation-solvent comprising benzyl alcohol; ii. treating the first APO-I-preparation mixture with hydrochloric acid; and iii. crystallizing the benzyl alcohol solvate of vilazodone hydrochloride.

In illustrative embodiments of the present invention, there is provided a process for preparation of vilazodone hydrochloride benzyl alcohol solvate described herein wherein the vilazodone hydrochloride benzyl alcohol solvate is Form APO-I.

In illustrative embodiments of the present invention, there is provided a process for preparation of vilazodone hydrochloride benzyl alcohol solvate described herein wherein the first APO-I-preparation-solvent further comprises dimethylformamide, acetic acid or mixtures thereof.

In illustrative embodiments of the present invention, there is provided a process for preparation of vilazodone hydrochloride benzyl alcohol solvate described herein wherein the hydrochloric acid is provided as a solution in an organic solvent.

In illustrative embodiments of the present invention, there is provided a process for preparation of vilazodone hydrochloride benzyl alcohol solvate described herein wherein the organic solvent is isopropanol.

In illustrative embodiments of the present invention, there is provided a process for preparation of vilazodone hydrochloride benzyl alcohol solvate described herein further comprising maintaining the crystallized benzyl alcohol solvate of vilazodone hydrochloride in a suspension at a temperature of about 30° C. to about 40° C.

In illustrative embodiments of the present invention, there is provided a crystalline benzyl alcohol solvate of vilazodone hydrochloride described herein wherein the molar ratio of vilazodone hydrochloride to benzyl alcohol is approximately 1:1.

In illustrative embodiments of the present invention, there is provided a Form APO-II of vilazodone hydrochloride benzyl alcohol solvate.

In illustrative embodiments of the present invention, there is provided a Form APO-II of vilazodone hydrochloride benzyl alcohol solvate described herein characterized by a PXRD diffractogram comprising peaks, in terms of degrees 2-theta, at approximately 10.5, 13.3, 15.8, 19.5, 21.2 and 24.7.

In illustrative embodiments of the present invention, there is provided a Form APO-II of vilazodone hydrochloride benzyl alcohol solvate described herein characterized by a PXRD diffractogram comprising peaks, in terms of degrees 2-theta, at approximately 9.2, 10.5, 13.3, 15.8, 18.6, 19.5, 20.2, 21.2, 22.3, 23.3, 24.7 and 25.4.

Figure 3:
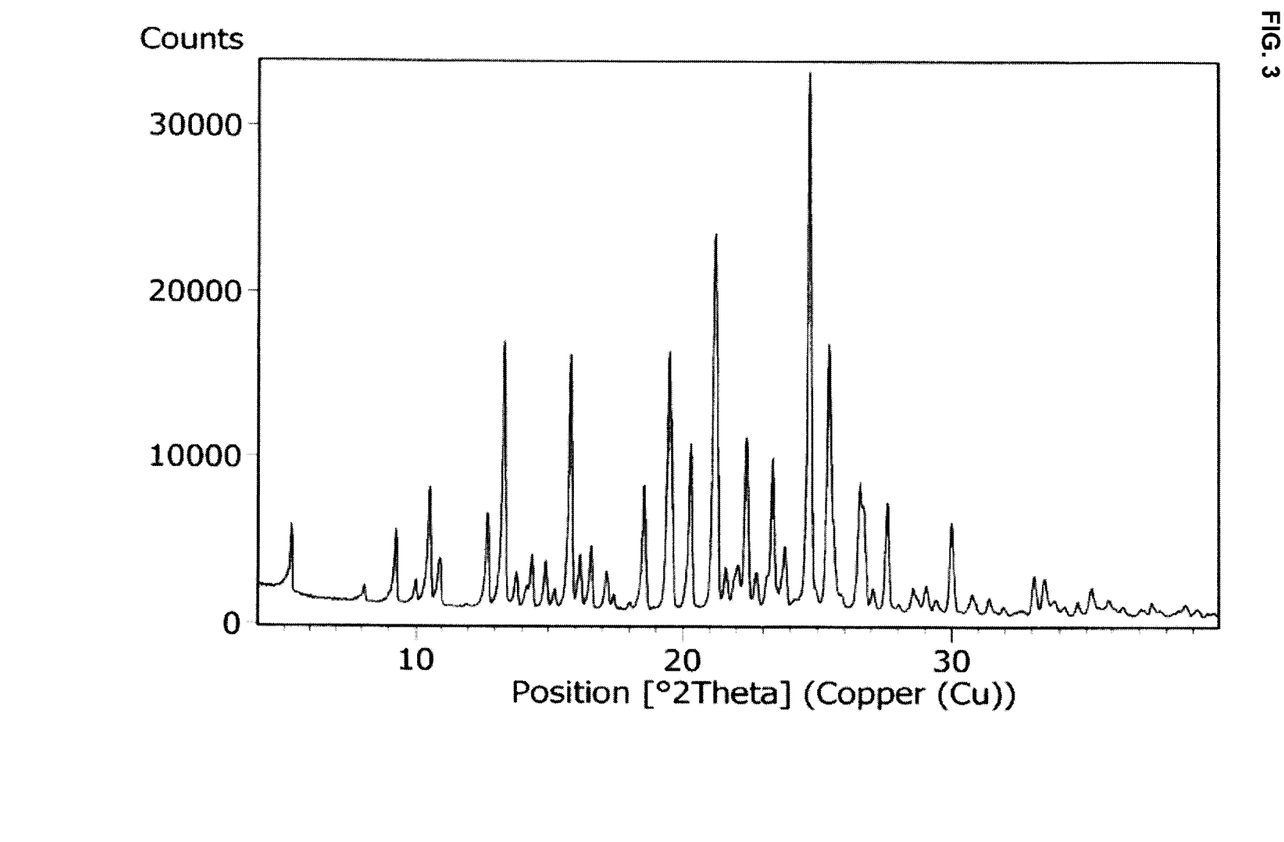
FIG. 3 is a powder X-ray diffraction (PXRD) diffractogram of APO-II

In illustrative embodiments of the present invention, there is provided a Form APO-II of vilazodone hydrochloride benzyl alcohol solvate described herein characterized by a PXRD diffractogram substantially similar to the PXRD diffractogram as depicted in FIG. 3.

In illustrative embodiments of the present invention, there is provided a Form APO-II of vilazodone hydrochloride benzyl alcohol solvate described herein characterized by a PXRD diffractogram as depicted in FIG. 3.

In illustrative embodiments of the present invention, there is provided a Form APO-II of vilazodone hydrochloride benzyl alcohol solvate described herein characterized by a 1% KBr FTIR spectrum comprising peaks, in terms of $cm^{-1}$, at approximately 3237, 2923, 2584, 2210, 1678, 1605, 1575, 1471, 1444, 1367 and 1231.

In illustrative embodiments of the present invention, there is provided a Form APO-II of vilazodone hydrochloride benzyl alcohol solvate described herein characterized by a 1% KBr FTIR spectrum comprising peaks, in terms of $cm^{-1}$, at approximately 3237, 2584, 2210, 1678, 1605, 1575, 1367 and 1231.

Figure 4:
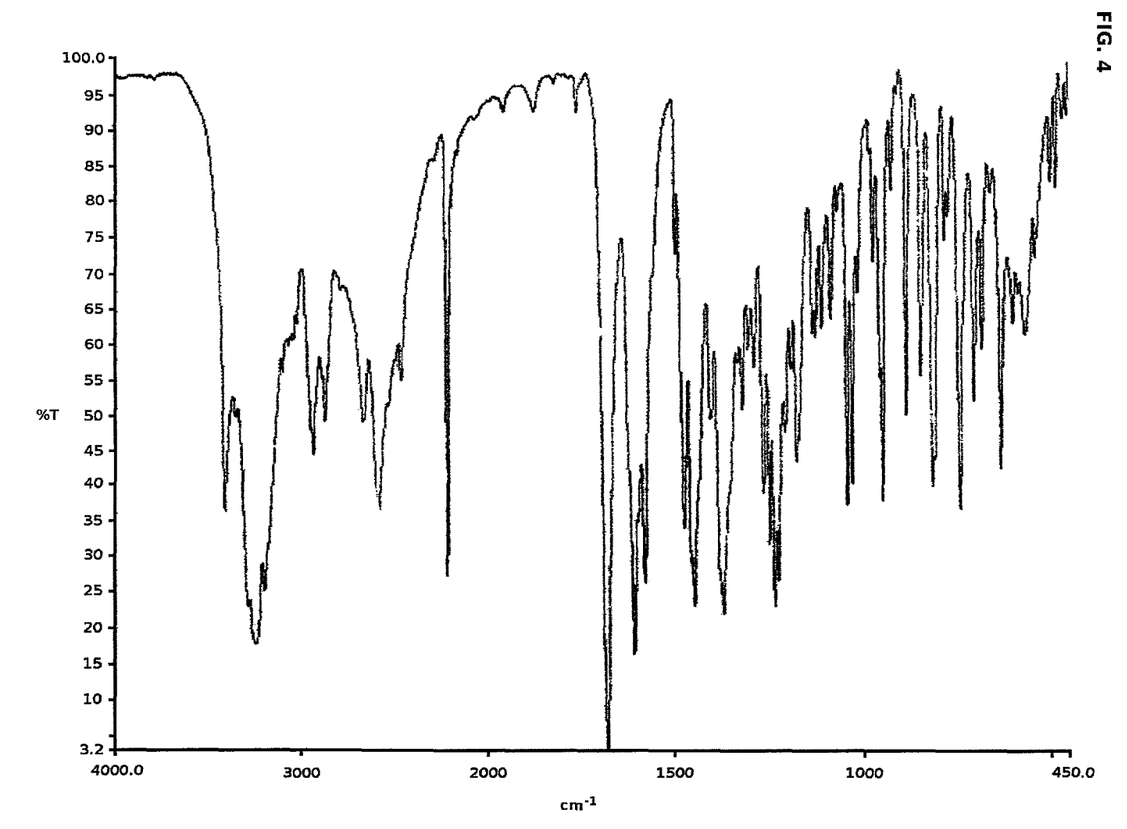
FIG. 4 is a Fourier Transform Infrared (FTIR) spectrum of APO-II

In illustrative embodiments of the present invention, there is provided a Form APO-II of vilazodone hydrochloride benzyl alcohol solvate described herein characterized by a FTIR spectrum substantially similar to the FTIR spectrum as depicted in FIG. 4.

In illustrative embodiments of the present invention, there is provided a Form APO-II of vilazodone hydrochloride benzyl alcohol solvate described herein characterized by a FTIR spectrum as depicted in FIG. 4.

In illustrative embodiments of the present invention, there is provided a pharmaceutical formulation comprising a Form APO-II vilazodone hydrochloride benzyl alcohol solvate described herein and a pharmaceutically acceptable excipient.

In illustrative embodiments of the present invention, there is provided a process for preparation of Form APO-II of vilazodone hydrochloride benzyl alcohol solvate, the process comprising: i. preparing a first APO-II-preparation-mixture of vilazodone free base and a first APO-II-preparation-solvent, the first APO-II-preparation-solvent comprising benzyl alcohol; ii. treating the first APO-II-preparation-mixture with hydrochloric acid to produce a second APO-II-preparation-mixture; iii. heating the second APO-II-preparation-mixture to a temperature of from about 80° C. to about 100° C.; and iv. crystallizing the Form APO-II vilazodone hydrochloride benzyl alcohol solvate.

In illustrative embodiments of the present invention, there is provided a process for preparation of Form APO-II of vilazodone hydrochloride benzyl alcohol solvate described herein wherein the first APO-II-preparation-solvent is selected from the group consisting of benzyl alcohol, dimethylformamide, acetic acid and mixtures thereof.

In illustrative embodiments of the present invention, there is provided a process for preparation of Form APO-II of vilazodone hydrochloride benzyl alcohol solvate described herein wherein the second APO-II-preparation-mixture is heated to a temperature of from about 90° C. to about 100° C.

In illustrative embodiments of the present invention, there is provided a process for preparation of Form APO-II of vilazodone hydrochloride benzyl alcohol solvate described herein further comprising maintaining the crystallized Form APO-II vilazodone hydrochloride benzyl alcohol solvate in a suspension at a temperature of from about 30° C. to about 40° C.

In illustrative embodiments of the present invention, there is provided a process for preparation of Form APO-II of vilazodone hydrochloride benzyl alcohol solvate comprising heating a third APO-II-preparation-mixture comprising Form APO-I of vilazodone hydrochloride benzyl alcohol solvate and benzyl alcohol to a temperature of from about 80° C. to about 100° C.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a PXRD diffractogram, the term "approximately" means that the peak may vary by ±0.2 degrees 2-theta of the subject value.

When used in reference to a peak in a FTIR spectrum, the term "approximately" means that the peak may vary by ±5 $cm^{-1}$ of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

The acceptable daily intake (ADI) for benzyl alcohol and its equivalents (benzoic acid, benzoate salts, benzaldehyde, benzyl acetate and benzyl benzoate) has been established by the World Health Organization at 5 mg/kg (JECFA, 2001).

The present invention encompasses the solvates isolated in pure form or when admixed with other materials, for example other isomers and/or polymorphic forms and/or salt forms or any other material.

Solvates have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

In one embodiment, the present invention comprises vilazodone hydrochloride benzyl alcohol solvate wherein the ratio of vilazodone hydrochloride to benzyl alcohol is approximately 1:0.5.

An illustrative PXRD diffractogram of Form APO-I vilazodone hydrochloride benzyl alcohol solvate obtained according to the conditions given in Example 7 is shown in FIG. 1. According to FIG. 1, the Form APO-I vilazodone hydrochloride benzyl alcohol solvate may have a reflection ("peak") at any one or more of the values expressed in degrees 2-theta given in Table 1. Although values are given in the tables below, the solvate may be defined by the claimed peaks and a particular claim may be limited to one peak only, or several peaks. The Form APO-I vilazodone hydrochloride benzyl alcohol solvate does not have to include all or even many of the peaks listed in Table 1. Some illustrative and non-limiting possible observations regarding relative intensities of the peaks are set out in Table 1.

TABLE 1

Form APO-I vilazodone hydrochloride benzyl alcohol solvate

| Peak (degrees 2-theta) | Relative Intensity (%) |
|---|---|
| 5.28 | 44.27 |
| 9.48 | 61.83 |
| 10.11 | 15.87 |
| 10.58 | 71.22 |
| 11.17 | 14.15 |
| 12.99 | 20.33 |
| 13.32 | 31.42 |
| 13.46 | 57.12 |
| 14.58 | 10.51 |
| 15.63 | 57.80 |
| 16.40 | 5.70 |
| 16.55 | 10.69 |
| 17.46 | 39.56 |
| 17.62 | 30.81 |
| 17.78 | 16.93 |
| 18.26 | 11.15 |
| 19.06 | 24.20 |
| 20.50 | 30.16 |
| 21.60 | 8.23 |
| 22.30 | 75.74 |
| 23.12 | 20.12 |
| 23.81 | 12.73 |
| 24.52 | 40.29 |
| 25.17 | 7.20 |
| 26.12 | 100.00 |
| 26.61 | 31.54 |

An illustrative FTIR spectrum of Form APO-I vilazodone hydrochloride benzyl alcohol solvate obtained according to the conditions given in Example 7 is shown in FIG. 2. According to FIG. 2, the Form APO-I vilazodone hydrochloride benzyl alcohol solvate may have an absorption band ("peak") at any one or more of the values expressed in $cm^{-1}$ given in Table 2. Some illustrative and non-limiting possible observations regarding peak intensity (% Transmission) of the peaks are set out in Table 2.

TABLE 2

Form APO-I vilazodone hydrochloride benzyl alcohol solvate

| Peak ($cm^{-1}$) | Intensity (% Transmission) |
|---|---|
| 3377.5 | 46.10 |
| 3228.4 | 40.75 |
| 3191.8 | 43.65 |
| 2945.0 | 65.30 |
| 2867.9 | 70.59 |
| 2667.1 | 67.97 |
| 2589.1 | 65.74 |
| 2451.3 | 74.75 |
| 2216.3 | 47.22 |
| 1675.8 | 9.95 |
| 1606.9 | 37.51 |
| 1579.2 | 40.22 |
| 1471.9 | 53.30 |
| 1443.2 | 42.70 |
| 1400.8 | 56.47 |
| 1380.2 | 38.64 |
| 1263.0 | 60.29 |
| 1232.6 | 41.00 |
| 1175.5 | 62.31 |

In an embodiment, the present invention relates to a process for preparation of vilazodone hydrochloride benzyl alcohol solvate comprising:
  i. preparing a first APO-I-preparation-mixture of vilazodone free base and a first APO-I-preparation-solvent, the first APO-I-preparation-solvent comprising benzyl alcohol;
  ii. treating the first APO-I-preparation-mixture with hydrochloric acid; and iii. crystallizing the benzyl alcohol solvate of vilazodone hydrochloride.

In an embodiment, the first APO-I-preparation-mixture is a solution or a suspension. The first APO-I-preparation-solvent may be benzyl alcohol alone or may further comprise acetic acid, DMF or mixtures thereof. In a particular embodiment, the first APO-I-preparation-solvent is benzyl alcohol.

Crystallizing the benzyl alcohol solvate may be induced by cooling and/or seeding. Following crystallization, a suspension may be formed and the suspension may be maintained at a temperature of about 30° C. to about 40° C. prior to isolation of the crystals.

The hydrochloric acid may be provided as a gas or as a solution in an organic or aqueous solvent. The organic solvent may be isopropanol.

In one embodiment, the present invention comprises vilazodone hydrochloride benzyl alcohol solvate wherein the molar ratio of vilazodone hydrochloride to benzyl alcohol is approximately 1:1.

An illustrative PXRD diffractogram of Form APO-II vilazodone hydrochloride benzyl alcohol solvate obtained according to the conditions given in Example 10 is shown in FIG. 3. According to FIG. 3, the Form APO-II vilazodone hydrochloride benzyl alcohol solvate may have a reflection ("peak") at any one or more of the values expressed in degrees 2-theta given in Table 3. Although values are given in the tables below, the solvate may be defined by the claimed peaks and a particular claim may be limited to one peak only, or several peaks. The Form APO-II vilazodone hydrochloride benzyl alcohol solvate does not have to include all or even many of the peaks listed in Table 3. Some illustrative and non-limiting possible observations regarding relative intensities of the peaks are set out in Table 3.

TABLE 3

Form APO-II vilazodone hydrochloride benzyl alcohol solvate

| Peak (degrees 2-theta) | Relative Intensity (%) |
|---|---|
| 5.26 | 11.52 |
| 9.24 | 12.76 |
| 9.99 | 3.90 |
| 10.51 | 20.57 |
| 10.88 | 7.74 |
| 12.70 | 15.46 |
| 13.32 | 47.84 |
| 13.79 | 6.11 |
| 14.38 | 9.10 |
| 14.87 | 8.94 |
| 15.80 | 46.89 |
| 16.16 | 9.40 |
| 16.56 | 12.23 |
| 17.15 | 7.91 |
| 18.55 | 22.48 |
| 19.47 | 47.02 |
| 20.25 | 32.54 |
| 21.18 | 67.13 |
| 21.59 | 7.10 |
| 22.34 | 31.78 |
| 22.70 | 7.42 |
| 23.31 | 26.15 |
| 23.75 | 11.36 |
| 24.68 | 100.00 |
| 25.41 | 51.96 |
| 26.61 | 23.73 |
| 27.57 | 21.88 |
| 29.98 | 18.09 |

An illustrative FTIR spectrum of Form APO-II vilazodone hydrochloride benzyl alcohol solvate obtained according to the conditions given in Example 10 is shown in FIG. 4. According to FIG. 4, the Form APO-II vilazodone hydrochloride benzyl alcohol solvate may have an absorption band ("peak") at any one or more of the values expressed in cm$^{-1}$ given in Table 4. Some illustrative and non-limiting possible observations regarding peak intensity (% Transmission) of the peaks are set out in Table 4.

TABLE 4

Form APO-II vilazodone hydrochloride benzyl alcohol solvate

| Peak (cm$^{-1}$) | Intensity (% Transmission) |
|---|---|
| 3402.3 | 36.55 |
| 3236.6 | 17.70 |
| 3189.9 | 25.28 |
| 2922.8 | 44.55 |
| 2863.1 | 49.30 |
| 2665.2 | 49.22 |
| 2584.4 | 35.80 |
| 2210.2 | 27.30 |
| 1678.4 | 3.09 |
| 1605.0 | 16.44 |
| 1575.1 | 26.45 |
| 1471.0 | 34.24 |
| 1444.1 | 23.21 |
| 1402.5 | 49.73 |
| 1367.4 | 22.15 |
| 1260.4 | 39.07 |
| 1244.6 | 31.90 |
| 1231.2 | 23.07 |
| 1221.4 | 26.65 |

In an embodiment, the present invention relates to a process for preparation of Form APO-II of vilazodone hydrochloride benzyl alcohol solvate comprising:

i. preparing a first APO-II-preparation-mixture of vilazodone free base and a first APO-II-preparation-solvent, the first APO-II-preparation-solvent comprising benzyl alcohol;

ii. treating the first APO-II-preparation-mixture with hydrochloric acid to produce a second APO-II-preparation-mixture;

iii. heating the second APO-II-preparation-mixture to a temperature of from about 80° C. to about 100° C. and crystallizing the vilazodone hydrochloride benzyl alcohol solvate.

In an embodiment, the first APO-II-preparation-mixture is a solution or a suspension. The first APO-II-preparation-solvent may be benzyl alcohol alone or may further comprise acetic acid, DMF or mixtures thereof. In a particular embodiment, the first APO-II-preparation-solvent is benzyl alcohol.

In an embodiment, the second APO-II-preparation-mixture is a solution or a suspension, which may or may not remain upon heating.

Crystallization of the Form APO-II benzyl alcohol solvate may occur spontaneously or may be induced by cooling and/or seeding. Following crystallization, a suspension may be formed and the suspension may be maintained at a temperature of about 30° C. to about 40° C. prior to isolation of the crystals.

The hydrochloric acid may be provided as a gas or as a solution in an organic or aqueous solvent. The organic solvent may be isopropanol.

In an embodiment, the present invention relates to a process for preparation of Form APO-II of vilazodone hydrochloride benzyl alcohol solvate comprising heating a third APO-II-preparation-mixture comprising Form APO-I of vilazodone hydrochloride benzyl alcohol solvate and benzyl alcohol to a temperature of from about 80° C. to about 100° C. The heating may be done for a suitable period of time from a minimum time of about 3 hours.

EXAMPLES

The following examples are illustrative of some of the embodiments of the invention described herein. These examples do not limit the spirit or scope of the invention in any way.

Powder X-Ray Diffraction Analysis: The data were acquired on a PANanalytical X-Pert Pro MPD diffractometer with fixed divergence slits and an X-Celerator RTMS detector. The diffractometer was configured in Bragg-Brentano geometry; data was collected over a 2-theta range of 3 to 40 using CuKα radiation at a power of 40 mA and 45 kV. CuKβ radiation was removed using a divergent beam nickel filter. A step size of 0.017 degrees was used.

Fourier Transform Infrared (FTIR) Analysis: The FTIR spectrum was collected at 4 cm$^{-1}$ resolution using a Perkin Elmer Paragon 1100 single beam FTIR instrument. The samples were intimately mixed in an approximately 1:100 ratio (w/w) with potassium bromide using an agate mortar and pestle to a fine consistency; the mixture was compressed in a pellet die at a pressure of 4 to 6 tonnes for a time period between 2 and 5 minutes. The resulting disk was scanned 4 times versus a collected background. Data was baseline corrected and normalized.

Example 1

1-[4-(5-Cyanoindol-3-yl)butyl]-4-(2-carbamoyl-benzofuran-5-yl)-piperazine (1 g) was dissolved in benzyl alcohol (10 ml) under inert gas atmosphere at 20-25° C. To the clear solution was added HCl in isopropanol (0.55 g, 1.2 eq). The resulting suspension was stirred for 20 h at 20-25° C. The suspension was then heated to 35° C. and maintained for 3 h. The solid was filtered, washed with acetone (2×5 mL) and dried at about 65° C. to afford 0.84 g hemi solvate of 1-[4-(5-cyanoindol-3-yl)butyl]-4-(2-carbamoyl-benzofuran-5-yl)-piperazine hydrochloride with benzyl alcohol. $^1$H NMR (DMSO-d$_6$) 11.47 (br s, 1H); 10.40 (br s, 1H); 8.10 (s, 1H); 8.05, 7.63 (br s, 2H); 7.55-7.50 (m, 2H); 7.45-7.39 (m, 3H); 7.32-7.25 (m, 2.5H); 7.23-7.20 (m, 1H); 5.10 (br s, 0.5H); 4.49 (s, 1H); 3.75-3.70 (m, 2H); 3.6-3.56 (m, 2H); 3.25-3.08 (m, 6H); 2.78 (t, 2H); 1.79-1.68 (m, 4H).

Example 2

1-[4-(5-Cyanoindol-3-yl)butyl]-4-(2-carbamoyl-benzofuran-5-yl)-piperazine (1.1 g) was dissolved in benzyl alcohol (10 ml) under inert gas atmosphere at 20-25° C. To the clear solution was added HCl in isopropanol (0.6 g, 1.2 eq). The resulting suspension was stirred for 20 h at 20-25° C. The suspension was heated to 35° C. and maintained for 3 h. The solid was filtered, washed with MTBE (2×5 ml) and dried at 65° C. to afford 0.88 g hemi solvate of 1-[4-(5-cyanoindol-3-yl)butyl]-4-(2-carbamoyl-benzofuran-5-yl)-piperazine hydrochloride with benzyl alcohol.

Example 3

1-[4-(5-Cyanoindol-3-yl)butyl]-4-(2-carbamoyl-benzofuran-5-yl)-piperazine (1 g) was dissolved in benzyl alcohol (10 ml) under inert gas atmosphere at 20-25° C. To the clear solution was added HCl in isopropanol (0.55 g, 1.2 eq). The resulting suspension was stirred for 20 h at 20-25° C. Ethyl acetate (5 ml) was added to the suspension followed by stirring for 3 h at 35° C. The solid was filtered, washed with ethyl acetate (2×5 ml) and dried at 65° C. to afford 0.9 g hemi solvate of 1-[4-(5-cyanoindol-3-yl)butyl]-4-(2-carbamoyl-benzofuran-5-yl)-piperazine hydrochloride with benzyl alcohol.

Example 4

1-[4-(5-Cyanoindol-3-yl)butyl]-4-(2-carbamoyl-benzofuran-5-yl)-piperazine (1 g) was dissolved in benzyl alcohol (10 ml) under inert gas atmosphere at 20-25° C. To the clear solution was added conc. HCl (0.31 g). The resulting suspension was stirred for 20 h at 20-25° C. The suspension was heated to 35° C. and maintained for 3 h. The solid was filtered, washed with MTBE (2×5 ml) and dried at 65° C. to afford 0.65 g hemi solvate of 1-[4-(5-cyanoindol-3-yl)butyl]-4-(2-carbamoyl-benzofuran-5-yl)-piperazine hydrochloride with benzyl alcohol.

Example 5

1-[4-(5-Cyanoindol-3-yl)butyl]-4-(2-carbamoyl-benzofuran-5-yl)-piperazine (1 g) in benzyl alcohol (5 ml) was heated under inert gas atmosphere to 45° C. To the suspension was added HCl in isopropanol (0.55 g, 1.2 eq) followed by cooling to 20-25° C. and stirring for about 20 h. The suspension was heated to 35° C. and maintained for 3 h. The solid was filtered, washed with MTBE (2×5 ml) and dried at 65° C. to afford 0.94 g hemi solvate of 1-[4-(5-cyanoindol-3-yl)butyl]-4-(2-carbamoyl-benzofuran-5-yl)-piperazine hydrochloride with benzyl alcohol.

Example 6

1-[4-(5-Cyanoindol-3-yl)butyl]-4-(2-carbamoyl-benzofuran-5-yl)-piperazine (1 g) was dissolved in a 1:1 mixture of DMF:benzyl alcohol (6 ml) under inert gas atmosphere at 20-25° C. To the clear solution was added HCl in isopropanol (0.55 g, 1.2 eq). The resulting suspension was stirred for about 20 h at 20-25° C. The suspension was heated to 35° C. and maintained for 3 h. The solid was filtered, washed with MTBE (2×5 ml) and dried at 65° C. to afford 0.9 g hemi solvate of 1-[4-(5-cyanoindol-3-yl)butyl]-4-(2-carbamoyl-benzofuran-5-yl)-piperazine hydrochloride with benzyl alcohol.

Example 7

1-[4-(5-Cyanoindol-3-yl)butyl]-4-(2-carbamoyl-benzofuran-5-yl)-piperazine (1 g) was dissolved in a 1:1 mixture of benzyl alcohol:AcOH (6 ml) under inert gas atmosphere and heated to 45° C. To the clear solution was added HCl in isopropanol (0.83 g, 1.2 eq) and the mixture was gradually cooled to 20-25° C. The resulting suspension was stirred for about 20 h. The suspension was heated to 35° C. and maintained for 3 h. The solid was filtered, washed with MTBE (2×5 ml) and dried at 65° C. to afford 0.95 g hemi solvate of 1-[4-(5-cyanoindol-3-yl)butyl]-4-(2-carbamoyl-benzofuran-5-yl)-piperazine hydrochloride with benzyl alcohol.

Example 8

1-[4-(5-Cyanoindol-3-yl)butyl]-4-(2-carbamoyl-benzofuran-5-yl)-piperazine (1 g) was dissolved in a 1:1 mixture of benzyl alcohol:DMF (6 ml) under inert gas atmosphere 20-25° C. To the clear solution was added HCl in isopropanol (0.49 g, 1.2 eq). The resulting suspension was stirred for about 20 h at 20-25° C. and heated to 30-35° C. and maintained for 3 h. The solid was filtered, washed with 1-propanol (2×5 ml) and dried at 65° C. to afford 0.98 g hemi solvate of 1-[4-(5-cyanoindol-3-yl)butyl]-4-(2-carbamoyl-benzofuran-5-yl)-piperazine hydrochloride with benzyl alcohol.

Example 9

1-[4-(5-Cyanoindol-3-yl)butyl]-4-(2-carbamoyl-benzofuran-5-yl)-piperazine (2 g) was dissolved in a 1:1 mixture of benzyl alcohol:DMF (6 ml) under inert gas atmosphere 20-25° C. To the clear solution was added HCl in isopropanol (0.98 g, 1.2 eq). The resulting suspension was stirred for about 20 h at 20-25° C. The solid was filtered, washed with MTBE (2×10 ml) and dried at 65° C. to afford 1.8 g hemi solvate of 1-[4-(5-cyanoindol-3-yl)butyl]-4-(2-carbamoyl-benzofuran-5-yl)-piperazine hydrochloride with benzyl alcohol.

Example 10

1-[4-(5-Cyanoindol-3-yl)butyl]-4-(2-carbamoyl-benzofuran-5-yl)-piperazine (4 g) in benzyl alcohol (36 ml) was heated to 35-40° C. under inert gas atmosphere. The clear solution was filtered through microfiber paper and washed with benzyl alcohol (4 ml). The filtrate was stirred at 20-25° C. for about 30 minutes. To the thin suspension was charged conc. HCl (0.91 g, 0.98 eq.) and a clear solution was obtained. Following stirring for about 10 minutes a thick suspension formed, which was allowed to stir at 20-25° C. for 17 hours. The suspension was heated to about 95° C. and stirred for about 6.5 hours whereupon the suspension became thin. The resulting suspension was cooled to 30-35° C. and stirred for about 1 hour. The solid was filtered, washed with benzyl alcohol (8 ml) and MTBE (3×8 ml) and dried in vacuo at 35-40° C. for about 3 hours to afford 4.5 g mono solvate of 1-[4-(5-cyanoindol-3-yl)butyl]-4-(2-carbamoyl-benzofuran-5-yl)-piperazine hydrochloride with benzyl alcohol.

Example 11

1-[4-(5-Cyanoindol-3-yl)butyl]-4-(2-carbamoyl-benzofuran-5-yl)-piperazine (25 g) was suspended in benzyl alcohol (250 ml) under inert gas atmosphere. The resulting suspension was charged with conc. HCl (0.91 g, 0.98 eq.) and after addition a clear solution was obtained. Following stirring for about 10 minutes a thick suspension formed, which was allowed to stir at 20-25° C. for 17 hours. The suspension was heated to about 95° C. and stirred for about 5 hours whereupon the suspension became thin. The resulting suspension was cooled to 30-35° C. and stirred for about 1 hour. The solid was filtered, washed with benzyl alcohol (50 ml) and MTBE (2×50 ml) and dried in vacuo at 20-25° C. for about 3 hours to afford 31.5 g mono solvate of 1-[4-(5-cyanoindol-3-yl)butyl]-4-(2-carbamoyl-benzofuran-5-yl)-piperazine hydrochloride with benzyl alcohol.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A crystalline benzyl alcohol solvate of vilazodone hydrochloride characterized by a PXRD diffractogram comprising peaks, in terms of degrees 2-theta at approximately 9.5, 10.6, 13.5, 15.6, 22.3 and 26.1 or at approximately 10.5, 13.3, 15.8, 19.5, 21.2, and 24.7.

2. The crystalline benzyl alcohol solvate of vilazodone hydrochloride of claim 1, wherein the crystalline benzyl alcohol solvate of vilazodone hydrochloride is characterized by a PXRD diffractogram comprising peaks, in terms of degrees 2-theta, at approximately 9.5, 10.6, 13.5, 15.6, 22.3, and 26.1, and
wherein the molar ratio of vilazodone hydrochloride to benzyl alcohol is approximately 1:0.5.

3. The crystalline benzyl alcohol solvate of vilazodone hydrochloride of claim 1, wherein the crystalline benzyl alcohol solvate of vilazodone hydrochloride is characterized by a PXRD diffractogram comprising peaks, in terms of degrees 2-theta, at approximately 10.5, 13.3, 15.8, 19.5, 21.2, and 24.7, and
wherein the molar ratio of vilazodone hydrochloride to benzyl alcohol is approximately 1:1.

4. The vilazodone hydrochloride benzyl alcohol solvate of claim 2, wherein the PXRD diffractogram further comprises peaks, in terms of degrees 2-theta, at approximately 5.3, 11.2, 14.6, 17.5, 19.1, 20.5, and 24.5.

5. The vilazodone hydrochloride benzyl alcohol solvate of claim 2 characterized by a PXRD diffractogram substantially similar to the PXRD diffractogram as depicted in FIG. 1.

6. The vilazodone hydrochloride benzyl alcohol solvate of claim 2 characterized by a 1% KBr FTIR spectrum comprising peaks, in terms of cm$^{-1}$, at approximately 3228, 2216, 1676, 1607, 1579, 1472, 1443, and 1380.

7. The vilazodone hydrochloride benzyl alcohol solvate of claim 6 characterized by a FTIR spectrum substantially similar to the FTIR spectrum as depicted in FIG. 2.

8. The vilazodone hydrochloride benzyl alcohol solvate of claim 3, wherein the PXRD diffractogram further comprises peaks, in terms of degrees 2-theta, at approximately 9.2, 18.6, 20.2, 22.3, 23.3, and 25.4.

9. The vilazodone hydrochloride benzyl alcohol solvate of claim 3 characterized by a PXRD diffractogram substantially similar to the PXRD diffractogram as depicted in FIG. 3.

10. The vilazodone hydrochloride benzyl alcohol solvate of claim 3 characterized by a 1% KBr FTIR spectrum comprising peaks, in terms of cm$^{-1}$, at approximately 3237, 2584, 2210, 1678, 1605, 1575, 1367, and 1231.

* * * * *